United States Patent [19]

Ogawa et al.

[11] Patent Number: 4,962,667

[45] Date of Patent: Oct. 16, 1990

[54] ULTRASONIC IMAGING APPARATUS

[75] Inventors: Toshio Ogawa; Kageyoshi Katakura, both of Tokyo; Shin-ich Kondo, Kodaira; Shin'ichiro Umemura; Hiroshi Ikeda, both of Hachioji; Noriyoshi Ichikawa, Ibaraki; Kinji Kuriyama, Matsudo, all of Japan

[73] Assignees: Hitachi, Ltd.; Hitachi Medical Corporation, both of Tokyo, Japan

[21] Appl. No.: 384,109

[22] Filed: Jul. 24, 1989

Related U.S. Application Data

[63] Continuation of Ser. No. 917,069, Oct. 8, 1986, abandoned.

[30] Foreign Application Priority Data

Oct. 9, 1985 [JP] Japan ............................ 60-223605
Oct. 9, 1985 [JP] Japan ............................ 60-223612

[51] Int. Cl.$^5$ .............................................. G01N 29/00
[52] U.S. Cl. ................................. 73/626; 128/661.01
[58] Field of Search ............................. 73/625, 626; 128/661.01; 367/105, 905

[56] References Cited

U.S. PATENT DOCUMENTS

| | | | |
|---|---|---|---|
| 4,180,790 | 12/1979 | Thomas | 73/626 |
| 4,235,111 | 11/1980 | Hassler | 73/626 |
| 4,351,038 | 9/1982 | Alais | 367/105 |
| 4,528,854 | 7/1985 | Shimazaki | 128/660 |
| 4,542,653 | 9/1985 | Liu | 128/660 |
| 4,641,660 | 2/1987 | Bele | 128/660 |
| 4,679,176 | 7/1987 | Ogawa et al. | 367/119 |

FOREIGN PATENT DOCUMENTS

| | | | |
|---|---|---|---|
| 0017383 | 10/1980 | European Pat. Off. | 128/660 |
| 2041525 | 9/1980 | United Kingdom | 128/660 |

Primary Examiner—John Chapman
Attorney, Agent, or Firm—Antonelli, Terry, Stout & Kraus

[57] ABSTRACT

In an ultrasonic imaging apparatus utilizing an array type ultrasonic probe having a number of arrayed probe elements, high frequency pulse signals subject to different delays are supplied to respective probe elements so as to generate an acoustic beam which converges to a predetermined focal point. When receiving a reflection acoustic beam resulting from the converging beam, a plurality of signal lines extending from respective probe elements are connected in common to set up a plurality of element groups each having a plurality of adjacently arrayed elements and respective signals derived from respective element groups are differently delayed and added together to generate a reception signal representative of a reception beam having a predetermined focal point.

9 Claims, 7 Drawing Sheets

FIG. 2

| FR | 15mm | 30mm | 45mm | 60mm OR MORE |
|---|---|---|---|---|
| A1 | N.C. | N.C. | N.C. | B10 |
| A2 | N.C. | N.C. | N.C. | B9 |
| A3 | N.C. | N.C. | N.C. | B8 |
| A4 | N.C. | N.C. | N.C. | B7 |
| A5 | N.C. | N.C. | N.C. | B6 |
| A6 | N.C. | N.C. | B10 | B5 |
| A7 | N.C. | N.C. | B9 | B5 |
| A8 | N.C. | N.C. | B8 | B4 |
| A9 | N.C. | N.C. | B7 | B4 |
| A10 | N.C. | N.C. | B6 | B3 |
| A11 | N.C. | B10 | B5 | B3 |
| A12 | N.C. | B9 | B4 | B2 |
| A13 | N.C. | B8 | B3 | B2 |
| A14 | N.C. | B7 | B2 | B2 |
| A15 | N.C. | B6 | B2 | B2 |
| A16 | B5 | B5 | B1 | B1 |
| A17 | B4 | B4 | B1 | B1 |
| A18 | B3 | B3 | B1 | B1 |
| A19 | B2 | B2 | B1 | B1 |
| A20 | B1 | B1 | B1 | B1 |
| A21 | B1 | B1 | B1 | B1 |
| A22 | B2 | B2 | B1 | B1 |
| A23 | B3 | B3 | B1 | B1 |
| A24 | B4 | B4 | B1 | B1 |
| A25 | B5 | B5 | B1 | B1 |
| A26 | N.C. | B6 | B2 | B2 |
| A27 | N.C. | B7 | B2 | B2 |
| A28 | N.C. | B8 | B3 | B2 |
| A29 | N.C. | B9 | B4 | B2 |
| A30 | N.C. | B10 | B5 | B3 |
| A31 | N.C. | N.C. | B6 | B3 |
| A32 | N.C. | N.C. | B7 | B4 |
| A33 | N.C. | N.C. | B8 | B4 |
| A34 | N.C. | N.C. | B9 | B5 |
| A35 | N.C. | N.C. | B10 | B5 |
| A36 | N.C. | N.C. | N.C. | B6 |
| A37 | N.C. | N.C. | N.C. | B7 |
| A38 | N.C. | N.C. | N.C. | B8 |
| A39 | N.C. | N.C. | N.C. | B9 |
| A40 | N.C. | N.C. | N.C. | B10 |

| INPUT | OUTPUT |
|---|---|
| A1 | B13 |
| A2 | B12 |
| A3 | B11 |
| A4 | B10 |
| A5 | B9 |
| A6 | B8 |
| A7 | B7 |
| A8 | B6 |
| A9 | B5 |
| A10 | |
| A11 | B4 |
| A12 | |
| A13 | B3 |
| A14 | |
| A15 | B2 |
| A16 | |
| A17 | |
| A18 | B1 |
| A19 | |
| A20 | |
| A21 | |
| A22 | |
| A23 | |
| A24 | |

| INPUT | OUTPUT |
|---|---|
| A1 | B18 |
| A2 | B17 |
| A3 | B16 |
| A4 | B15 |
| A5 | B14 |
| A6 | B13 |
| A7 | B12 |
| A8 | B11 |
| A9 | B10 |
| A10 | B9 |
| A11 | B8 |
| A12 | B7 |
| A13 | B6 |
| A14 | B5 |
| A15 | B4 |
| A16 | B3 |
| A17 | |
| A18 | B2 |
| A19 | |
| A20 | B1 |
| A21 | |
| A22 | |
| A23 | |
| A24 | |

ULTRASONIC IMAGING APPARATUS

This application is a continuation of application Ser. No. 917,069, filed Oct. 8, 1986, now abandoned.

BACKGROUND OF THE INVENTION

This invention relates to an ultrasonic imaging apparatus used for medical diagnosis, material crack detection and marine investigation.

In order to raise the level of image performance represented by image signal to noise ratio and azimuth resolution in an ultrasonic imaging apparatus based on an array type probe in which an ultrasonic beam is converged to form an image by controlling phase and amplitude of transmission/reception signals of individual elements constituting the array, a great number of elements need to be allocated to a transmission/reception aperture of the probe by increasing the number of signal channels undertaking simultaneous signal processing. Disadvantageously, awful expensiveness results from an increase in the number of signal channels especially reception channels.

A countermeasure to this problem is disclosed in, for example, U.S. Pat. No. 4,235,111. In this patent, among a great number of elements within a reception aperture, a plurality of elements near the center are connected in common and signals of the plural elements are treated as a single channel signal. For elements at a peripheral portion of the reception aperture, on the other hand, such elements as symmetrically positioned are paired and connected in common so that each pair provides a single channel signal. The respective channel signals are separately delayed and controlled in phase, and the phase controlled signals are added together. The resultant signal stands for a reception signal representative of a reception beam having a focal point at a desired depth.

When advancing the expediency proposed by the above patent by increasing the number of elements to be connected in common to the same channel, however, the magnitude of an unwanted response due to a side lobe of a reception beam is increased in proportion to an increase in the number of elements commonly connected to the same channel, thus degrading the signal to noise ratio of the image.

SUMMARY OF THE INVENTION

An object of this invention is to provide an inexpensive ultrasonic imaging apparatus which can exhibit high image performance over the overall working area covering a near range and a far range.

To accomplish the above object, an ultrasonic imaging apparatus according to the invention utilizes an array type probe having a plurality of arrayed transducer elements, wherein individual elements are supplied with transmission signals respectively subject to differently specified delays to generate a transmission beam which converges to a predetermined focal point and, in the mode of reception of waves, a signal line connection circuit is used to set up a plurality of element groups each having a plurality of adjacently arrayed elements which are electrically interconnected together, by connecting in common signal lines, among those connected to the individual elements, which extend from the adjacently arrayed elements and output signals from the signal line connection circuit are differently delayed and added together to generate a reception signal representative of a reception beam having a predetermined focal point. By making common connection patterns or delay patterns applied to the respective elements different for transmission and reception in this manner, the magnitude of a side lobe in a round-trip response can be suppressed, thereby ensuring that an image of a high signal to noise ratio can be obtained.

According to another feature of the invention, the focal distance of the reception beam is sequentially changed and in synchronism therewith, the pattern of common connection set up by the signal line connection circuit is also changed sequentially. For delaying the reception beam, on the other hand, a sample hold circuit is used and the timing for changing-over the common connection pattern is set to precede, by a predetermined time interval, the sample timing of the sample hold circuit to thereby prevent a noise caused by the change-over from interfering with the reception signal.

According to still another feature of the invention, an incremental delay circuit is connected between the signal line connection circuit and each element and the reception signals of respective elements in each element group are made to slightly differ from each other in delay time by means of the incremental delay circuit.

BRIEF DESCRIPTION OF THE DRAWINGS

FIG. 2 shows input/output connections of signal lines in the FIG. 1 embodiment;

DESCRIPTION OF THE PREFERRED EMBODIMENTS

The invention will now be described by way of example with reference to the accompanying drawings.

Figure 1:
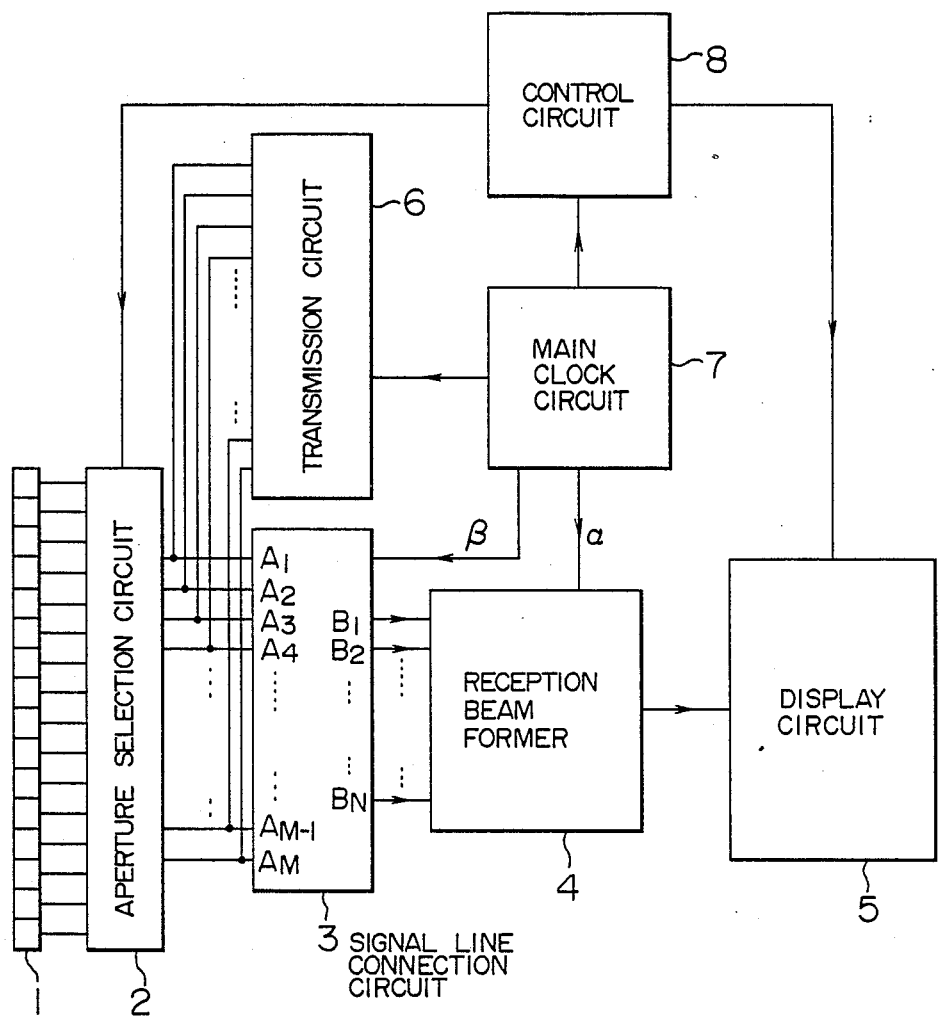
FIG. 1 is a block diagram showing an ultrasonic imaging apparatus according to an embodiment of the invention.

As diagrammatically shown in FIG. 1, in an ultrasonic imaging apparatus embodying the invention, signal lines extending from individual elements of an array type ultrasonic probe 1 are first led for selection to an aperture selection circuit 2 and branched to two paths one of which is connected to a transmission circuit 6 and the other is connected through a signal line connection circuit 3 to a reception beam former 4 which produces a reflection image signal to be displayed by a display circuit 5. The whole arrangement operates synchronously on the basis of signals from a main clock circuit 7. In particular, the aperture selection circuit 2 is synchronized with the display circuit 5 by means of a control circuit 8. In this embodiment, the focal point of the reception beam is changed at, for example, four steps of 15 mm, 30 mm, 45 mm and 60 mm or more. In this instance, the signal line connection circuit 3 operates as will be explained below with reference to FIG. 2 showing the connection relationship in the signal line connection circuit 3 between input signal lines $A_1$ to $A_{40}$ and output signal lines $B_1$ to $B_{10}$ arranged for respective focal distances. In this example, a line extending from the focal point is normal to the array of transducer elements at a point between elements respectively connected to the input signal lines $A_{20}$ and $A_{21}$. Taking connections for the focal distance $F_R$ being 45 mm, for instance, the number of input signals or elements respectively connected to the output signal lines $B_1$ to $B_{10}$ is 10, 4, 2, 2, 2, 2, 2, 2 and 2, indicating that the number decreases or does not change from the leg point of the normal toward the edge of the transmission/reception aperture. The monotonic decrease in the number of elements connected commonly is held true for the other focal distances but the pattern of connection is changed in accordance with the focal distance as shown in FIG. 2.

The reception beam former 4 comprises a delay circuit for differently delaying signals on the signal lines $B_1$ to $B_{10}$ adapted for common connection, an adder for adding together the delayed signals and a detector for diode-detection of a resultant signal. The amount of delay is changed for respective channels of the reception beam former 4 when the focal distance is changed to 15 mm, 30 mm, 45 mm or 60 mm or more.

In the mode of beam transmission, on the other hand, the common connection of elements as above is not established but the transmission circuit supplies, to respective elements in use for beam transmission, high frequency pulse currents which are respectively subject to different amounts of delay. Preferably, ten elements $A_{16}$ to $A_{25}$ are operated to transmit an ultrasonic beam which converges to a focal distance of 20 mm and thereafter, a beam reception with the 15 mm focal distance and another beam reception with the 30 mm focal distance are carried out successively. Subsequently, thirty elements $A_6$ to $A_{35}$ are operated to transmit an ultrasonic beam which converges to a focal distance of 50 mm and thereafter, a beam reception with the 45 mm focal distance and another beam reception with the 60 mm or more focal distance are performed successively.

Figures 3, 4, 8:
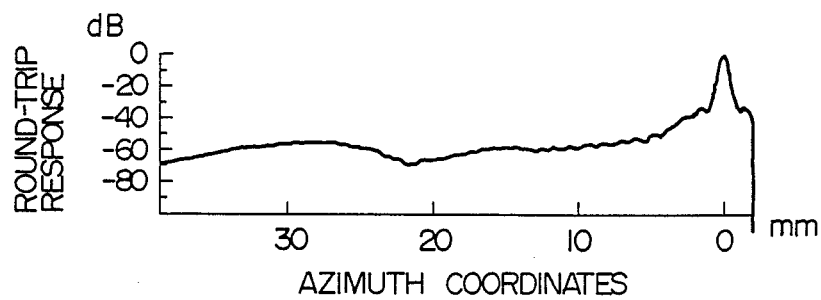
FIGS. 3, 5 and 6 graphically illustrate directivity of a round-trip response, a reception response and a transmission response, respectively.
FIG. 4 shows input/output connections of signal lines used for obtaining the characteristics of FIGS. 3, 5 and 6.
FIG. 8 shows input/output connections of signal lines used for obtaining the characteristic of FIG. 7.
Figure 5:
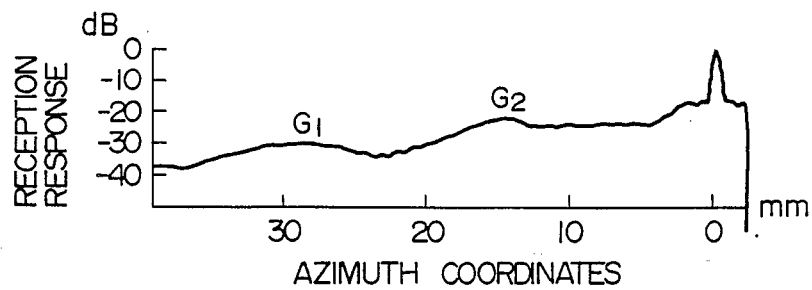
Figure 6:
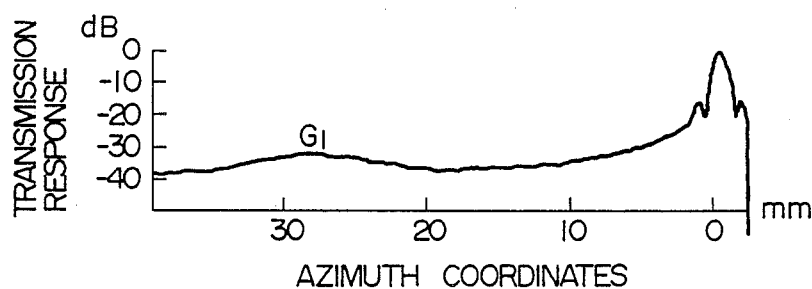

As described above, upon formation of transmission/reception beams, the common connection of signal lines of respective elements is applied to only reception beam focussing but for transmission beam focussing, respective elements are independently applied with different delay times. This configuration is advantageous as will be described below with reference to FIGS. 3 to 7. More particularly, when physical dimensions are exemplarily set such that the ultrasonic frequency is 3.5 MHz, the focal distance is 80 mm, the element width is 0.8 mm, the number of elements within a transmission aperture is 30, the number of elements within a reception aperture is 48, and the number m(n) of commonly connected signal lines in n-th set starting from the center of the aperture is so distributed as to provide m(1)=7, m(2)=3, m(3)=m(4)=m(5)=2 and m(n)=1 (n≧6) along a half of the aperture, a round-trip response as shown in FIG. 3 is obtained, where abscissa represents azimuth distance from the beam center and ordinate represents relative sensitivity. Thus, FIG. 3 shows directivity of a round-trip response. For this beam transmission/reception, the input/output relation is set up as shown in FIG. 4 in the signal line connection circuit 3 of FIG. 1. If a beam reception is performed with 48 elements, 24 kinds of delay times will be applied to reception signals of the respective elements. Without the common connection of adjacent elements established by the signal line connection circuit 3, a reception circuit of 24 channels would therefore be needed. By virtue of the circuit 3, however, the number of channels can be decreased to 13 in the example represented by FIGS. 3 and 4. Specifically, the number of channels leading to the reception beam former 4 can be decreased by 45% and sensitivity of a side lobe at an azimuth distance of 10 mm or more is about −60 dB, exhibiting a high acoustic signal to noise ratio. The above illustrated sensitivity can be achieved with the common connection technique applied to only the reception signal lines by taking advantage of the fact that an unwanted response $G_2$ caused by the common connection in a directivity characteristic of reception response as shown in FIG. 5 occurs at a position which corresponds to a valley position in a directivity characteristic of transmission response as shown in FIG. 6. In these figures, $G_1$ denotes a grating lobe.

Figure 7:
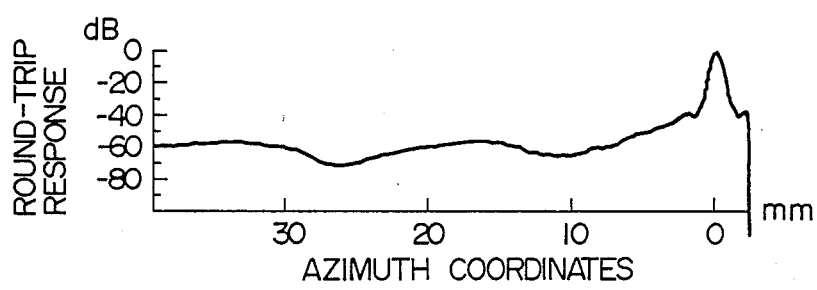
FIG. 7 is a graphical representation showing directivity of a round-trip response in comparison with that of FIG. 3.

As a comparison, an attempt is made to obtain an acoustic signal to noise ratio comparable to that of FIG. 3 by applying the common connection to both the transmission and reception under the condition that the number m(n) of commonly connected signal lines is so distributed as to provide m(1)=5, m(2)=m(3)=2 and m(n)=1 (n≧4) as indicated in FIG. 8. A resulting characteristic is shown in FIG. 7. As will be seen from FIG. 7, when signal lines for the beam transmission are commonly connected in the same pattern as signal lines for the beam reception, both the transmission and reception beams are attended with a side lobe at the same azimuth distance. Accordingly, when the number of channels is decreased to a great extent by the common connection of signal lines, a high level of an unwanted response takes place in the round-trip response. Therefore, in order to sustain an acoustic signal to noise ratio comparable to that of the example of FIGS. 3 and 4, the reduction in the number of channels by the common connection of signal lines must be limited to 25%, indicating that 24 channels are allowed to be reduced to 18 channels.

Although in the foregoing embodiment the number of channels leading to the reception beam former can be decreased greatly and the high acoustic signal to noise ratio can be obtained by connecting adjacently arrayed probe elements in common only in the mode of reception of waves, a high acoustic signal to noise ratio may also be obtained by commonly connecting adjacent probe elements only in the mode of transmission of waves and applying different delays to signals of respective elements in the mode of reception of waves. If the apparatus becomes more costly by applying delays to the transmission signals than by doing so in connection with the reception signals, then this modification will advantageously be adopted to reduce the cost of the whole of apparatus.

Figure 9A:
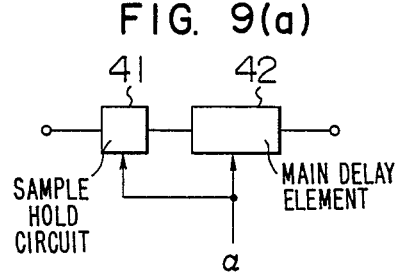
FIG. 9(a) illustrates a delay circuit.
Figure 9B:
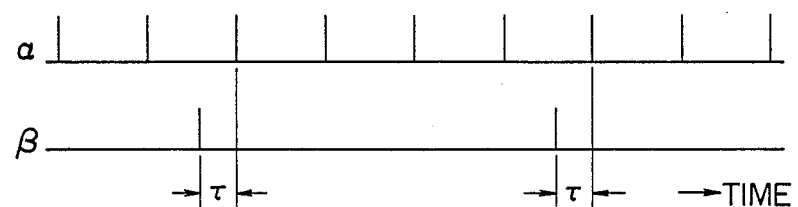
FIG. 9(b) is a time chart illustrative of a control timing for the delay circuit.

In the embodiment of FIGS. 1 and 2, the focal distance of reception beam is switched from 15 mm to 30 mm or from 45 mm to 60 mm or more during reception following one transmission. Generally, this focal distance switching is based on dynamic focussing in which the signal line connection circuit 3 in the embodiment of FIGS. 1 and 2 is operated to switch a common connection of elements to another common connection of elements in synchronism of the change of focal distance. As a result, a noise caused by the switching of connection interferes with the reception signal and ultimately, it will disadvantageously be displayed. To eliminate this problem, the reception beam former 4 comprises a delay circuit whose one channel component is schematically illustrated in FIG. 9(a). The delay circuit has a main delay element 42, for example, in the form of switched capacitor memories connected in tandem and a sample hold circuit 41 preceding the element 42. The reception signal is sampled sequentially by the sample hold circuit 41 and delayed for delivery by the main delay element 42. A control signal α supplied from the main clock circuit 7 controls the sample timing of the sample hold circuit 41 and the activation of the main delay element 42. On the other hand, the signal line connection circuit 3 changes the common connection at the timing of a control signal β supplied from the main clock circuit 7. As shown in FIG. 9(b), the time relationship between the control signals α and β is determined such that the control signal β precedes the control signal α by a time interval τ. The time interval τ is set to be long enough to exceed at least the duration of a noise due to switching by the signal line connection circuit 3. Accordingly, even when the focal distance of the reception beam is changed and the signal line connection circuit 3 switches its connections in synchronism with the switching of focal distance during a beam reception following one beam transmission, the output of the reception beam former 4 is not affected by the noise due to the switching by the circuit 3.

Figure 10:
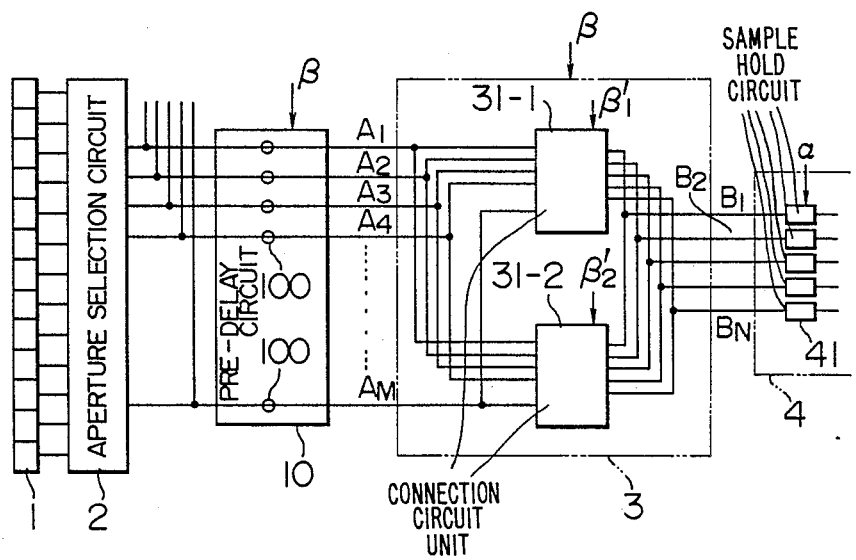
FIG. 10 is a fragmentary block diagram showing another embodiment of the invention.

In the previous embodiment, reception signals from collective elements connected in common by means of the signal line connection circuit 3 are all subject to the same amount of delay. With an auxiliary incremental delay circuit preceding the signal line connection circuit 3, however, reception signals of respective elements can be delayed differently. FIG. 10 shows another embodiment to this effect.

Figure 11:
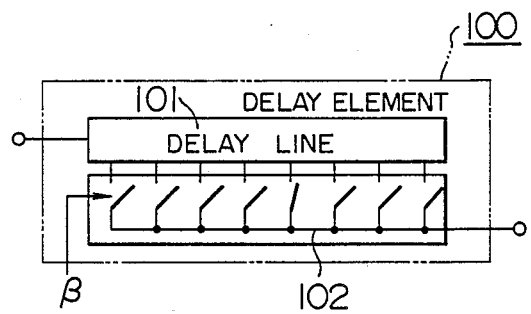
FIGS. 11 and 13 are circuit diagrams of components of the FIG. 10 embodiment.

Signal lines from elements 1 are selected by the aperture selection circuit 2 and connected to the signal line connection circuit 3 through an incremental delay circuit 10. The incremental delay circuit 10 has delay elements 100 provided for individual channels. Each delay element 100 includes, as shown in FIG. 11, an LC delay line 101 having a number of taps and a multiplexer 102 which selects one of the plurality of taps and delivers a selected signal. Output signal lines $A_1$ to $A_M$ extending from the incremental delay circuit 10 are selectively interconnected by means of the signal line connection circuit 3 so as to be grouped into N signal lines $B_1$ to $B_N$ which in turn are led to respective main delay circuits of the reception beam former 4. The remaining components are identical to those of FIG. 1 and are not illustrated in FIG. 10.

Figure 12A:
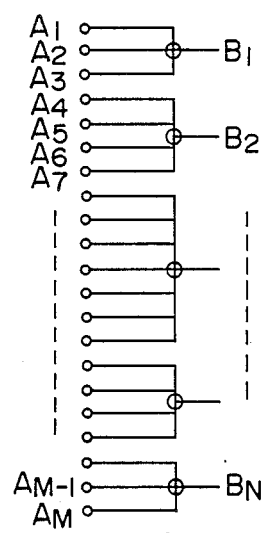
FIGS. 12(a) and 12(b) are connection diagrams showing input/output signal line connections in the FIG. 10 embodiment.
Figure 12B:
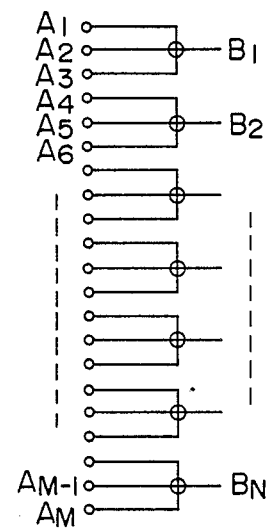
Figure 13:
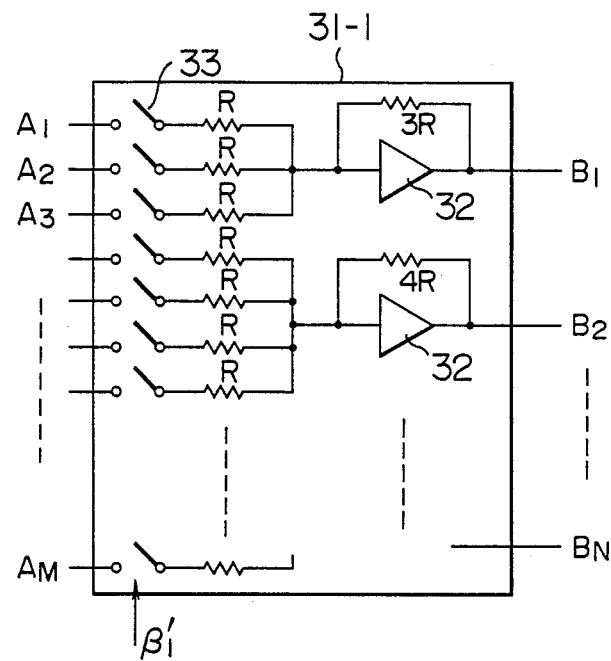
Figure 14:
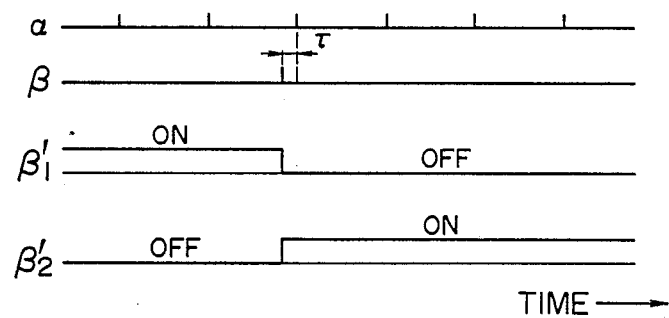
FIG. 14 is a time chart illustrative of control timings for the FIG. 10 embodiment.

In this embodiment, each delay element 100 of the incremental delay circuit 10 can apply slightly different delay times to reception signals from individual elements. Therefore, the common connection can be applied to signal lines of all the elements within a reception aperture without adversely affecting the round-trip response. This permits more reduction in the number N of output signal lines from the signal line connection circuit 3 or the number of channels for the reception beam former 4, as compared to the example of FIGS. 1 and 2. The N output signal lines can be connected in common in various patterns which are changeable, as in the example of FIGS. 1 and 2, each time the focal distance is changed. FIGS. 12(a) and 12(b) illustrate examples of the changeable common connection pattern. In order to switch common connections, the signal line connection circuit 3 includes a plurality of connection circuit units each of which is operated for each pattern of common connection. Exemplarily, two connection circuit units 31-1 and 31-2 are illustrated in FIG. 10. FIG. 13 details one connection circuit unit. A plurality of operational amplifiers 32 are each connected with a feedback resistor (3R, 4R) and connected to input resistors (R) the number of which is determined in accordance with a pattern of a common connection of signal lines. The input resistors are respectively connected to the input signal lines $A_1$ to $A_N$ through a switch 33. When a control signal $\beta_1'$ is high, the switches 33 are turned on simultaneously and each operational amplifier 32 produces an output signal representative of addition of reception signals from elements connected in common. As in the example of FIGS. 1 and 2, the number M of elements used for beam reception and the number N of output signal lines connected in common are varied with a focal distance set for beam reception and the number of operational amplifiers 32 differs from one unit to another correspondingly. The plurality of connection circuit units are connected in parallel and when their control signals ($\beta_1'$ and $\beta_2'$ in the example of FIG. 10) are alternately turned on, patterns of common connection of signal lines are switched over. Upon switching the focal distance of reception beam, contacts of the multiplexer 102 included in the incremental delay circuit shown in FIG. 11 must be switched. The foal distance and the control signal $\beta_1'$ or $\beta_2'$ are switched simultaneously under the direction of the control signal β. Specifically, the switching is effected synchronously with the control signal β which, as indicated in FIG. 9(b), precedes by the time interval τ the control signal α which prescribes the sample timing of the initial stage sample hold circuit 41 in the delay circuit included in the reception beam former 4. Thus, these control signals α, β, $\beta_1'$ and $\beta_2'$ are rendered on in accordance with the time relationship indicated in FIG. 14. In this embodiment, the time interval τ is set to be long enough to exceed either one of the duration of a noise due to switching of the multiplexer 102 included in the incremental delay circuit 10 or the duration of a noise due to connection switching (effected by turning on or off the switches 33) in the signal line connection circuit 3. In this way, the noises caused by switching can be prevented from interfering with the output of the reception beam former 4 and an image of a high signal to noise ratio can be obtained.

We claim:

1. An ultrasonic imaging apparatus comprising:
  an array type ultrasonic probe having a plurality of arrayed probe elements;
  beam transmission means for supplying to at least a part of said probe elements transmission signals which are respectively subject to differently specified delays so as to generate an acoustic beam which converges to a predetermined focal point;
  signal line connection means for setting up a plurality of element groups each having a plurality of adjacently arrayed probe elements which are electrically interconnected together, by connecting a plurality of signal lines respectively extending from said adjacently arrayed probe elements, the number of said plurality of adjacently arrayed probe elements in respective ones of said element groups being decreased in a direction from a center of a reception aperture of said array type ultrasonic probe toward an edge of the reception aperture thereof, said element groups being respectively connected to output signal lines of said signal line connection means; and reception beam former means for applying different delays to respective signals on output signal lines of said signal line connection means and adding delayed signals together so as to form a reception signal representative of a reception beam having a predetermined focal point.

2. An ultrasonic imaging apparatus according to claim 1 wherein said reception beam former means has a function of changing the focal distance of a reception beam, and said signal line connection means has a function of changing the pattern of said element groups in synchronism with changing the focal distance.

3. An ultrasonic imaging apparatus according to claim 1 further comprising incremental delay means, connected between said probe elements and said signal line, connection means, for applying slightly different delay times to respective reception signals of said probe elements.

4. An ultrasonic imaging apparatus comprising:

an array type ultrasonic probe having a plurality of arrayed probe elements;

beam transmission means for applying to at least a part of said probe elements transmission signals which are respectively subject to differently specified delays so as to generate an acoustic beam which converges to a predetermined focal point;

signal line connection means for setting up a plurality of element groups each having a plurality of adjacently arrayed probe elements which are electrically interconnected together, by connecting a plurality of signals lines. respectively extending from said adjacently arrayed probe elements and for sequentially changing the pattern of said element groups, said element groups being respectively connected to output signal lines of said signal line connection means;

reception beam former means including delay means, comprised of sample hold mans for sequentially repeating a sampling operation at a sample timing, for applying different delays to respective signals on output signal lines of said signal line connection means, said reception former means being operative to add delayed signals together so as to form a reception signal representative of a reception beam having a predetermined focal point and to sequentially change the focal distance of said focal points; and timing control means for causing said signal line connection means to change the pattern of said element groups at a specified timing which precedes, by a predetermined time interval set to be long enough to exceed the duration of a noise, one of the sequential sample timings of said sample hold means.

5. An ultrasonic imaging apparatus according to claim 4 wherein said predetermined time interval determined by said timing control means is set to be long enough to exceed the duration of a noise due to changing the pattern of said element groups by said signal line connection means.

6. An ultrasonic imaging apparatus according to claim 4 further comprising incremental delay means, connected between said probe elements and said signal line connection means, for applying slightly different delay times to respective reception signals of said probe elements and changing the amount of delay in synchronism with changing the focal distance by said reception beam former means.

7. An ultrasonic imaging apparatus according to claim 6 wherein said predetermined time interval determined by said timing control means is set to be long enough to exceed either one of the duration of a noise due to changing the pattern of said element groups by said signal line connection means or the duration of a noise due to changing the delay amount by said incremental delay means.

8. An ultrasonic imaging apparatus according to claim 4, wherein the number of said plurality of adjacently arrayed probe elements of respective ones of said element groups is decreased in a direction from a center of a reception aperture of said array type ultrasonic probe toward an edge of the reception aperture thereof.

9. An ultrasonic imaging apparatus comprising:

an array type ultrasonic probe having a plurality of arrayed probe elements;

beam transmission means for applying to at least a part of said probe elements transmission signals which are respectively subject to differently specified delays so as to generate an acoustic beam which converges to a predetermined transmission focal point; and reception means for receiving signals in response to the acoustic beam converged to the predetermined transmission focal point, the reception means including:

(a) signal line connection means for setting up a plurality of element groups each having a plurality of adjacently arrayed probe elements which are electrically interconnected together, by connecting a plurality of signal lines respectively extending from said adjacently arrayed probe elements and for sequentially changing the pattern of said element groups, said element groups being respectively connected to output signal lines of said signal line connection means;

(b) reception beam former means including delay means, comprised of sample hold means for sequentially repeating a sampling operation at a sample timing, for applying different delays to respective signals on output signal lines of said signal line connection means, said reception former means being operative to add delayed signals together so as to form reception signals representative of reception beams having different predetermined reception focal points; and (c) timing control means for causing said signal line connection means to change the pattern of said element groups for receiving signals in response to the acoustic beam converged in the predetermined transmission at a specified timing which precedes, by a predetermined time interval set to be long enough to exceed the duration of a noise, one of the sequential sample timings of said sample hold means.

* * * * *